US007833518B2

(12) United States Patent
Sakuma et al.

(10) Patent No.: US 7,833,518 B2

(45) Date of Patent: Nov. 16, 2010

(54) ANIONIC SURFACTANT POWDER

(75) Inventors: Yasumitsu Sakuma, Wakayama (JP); Kazuhito Miyoshi, Wakayama (JP)

(73) Assignee: Kao Corporation, Tokyo (JP)

( * ) Notice: Subject to any disclaimer, the term of this patent is extended or adjusted under 35 U.S.C. 154(b) by 974 days.

(21) Appl. No.: 10/502,404

(22) PCT Filed: Jan. 29, 2003

(86) PCT No.: PCT/JP03/00848

§ 371 (c)(1),
(2), (4) Date: Jul. 26, 2004

(87) PCT Pub. No.: WO03/064577

PCT Pub. Date: Aug. 7, 2003

(65) Prior Publication Data

US 2005/0106118 A1 May 19, 2005

(30) Foreign Application Priority Data

Jan. 29, 2002 (JP) ............................. 2002-019368

(51) Int. Cl.
*A61K 8/34* (2006.01)

(52) U.S. Cl. .................... 424/70.24; 510/127; 510/457; 510/492

(58) Field of Classification Search ....................... None
See application file for complete search history.

(56) References Cited

U.S. PATENT DOCUMENTS 4,808,641 A 2/1989 Yagi et al.
5,362,479 A * 11/1994 Breitzke et al. ............... 424/49

FOREIGN PATENT DOCUMENTS

| | | |
|---|---|---|
| EP | 572 957 | 12/1993 |
| EP | 1 201 740 | 5/2002 |
| GB | 1174248 | 12/1969 |
| JP | 54-52196 | 4/1979 |
| JP | 62-191417 | 8/1987 |
| JP | 62-191419 | 8/1987 |
| JP | 5-331496 | 12/1993 |
| JP | 8-3593 | 1/1996 |
| JP | 2001-327866 | 11/2001 |

OTHER PUBLICATIONS

Michael F. Cox, "The Effect of 'Peaking' the Ethylene Oxide Distribution on the Performance of Alcohol Ethoxylates and Ether Sulfates", JAOCS. vol. 67. No. 9, Sep. 1990, pp. 599-604.
http://de.wikipedi.org/w/index.php?oldid=59325855—Wikipedia. de Stichwort: "Mittelwert", pp. 1-12.

* cited by examiner

*Primary Examiner*—Robert A Wax
*Assistant Examiner*—Hasan S Ahmed
(74) *Attorney, Agent, or Firm*—Oblon, Spivak, McClelland, Maier & Neustadt, L.L.P.

(57) ABSTRACT

To provide an anionic surfactant powder comprising a polyoxyalkylene ether sulfate which powder has high stability in hard water, high low-temperature solubility and is improved in powder characteristics such as caking characteristics, and a method of producing the anionic surfactant powder. An anionic surfactant powder comprising polyoxyalkylene alkyl ether sulfates in which the average addition mol number of alkylene oxides is 0.05 to 2, wherein the content of the polyoxyalkylene alkyl ether sulfates provided with alkylene oxides added thereto in an amount of 4 mol or more is 30 % by weight or less based on the total anionic surfactant, an anionic surfactant powder further comprising a water-soluble inorganic salt, a method of producing each of these anionic surfactant powders, and a detergent composition and a cement additive comprising these anionic surfactant powders.

16 Claims, No Drawings

ANIONIC SURFACTANT POWDER

ART FIELD OF INVENTION

The present invention relates to an anionic surfactant powder which can be preferably used for detergents, emulsifiers and the like, is superior in stability in hard water and low-temperature solubility and is improved in powder characteristics such as caking characteristics, to a method of producing the anionic surfactant powder simply and efficiently and to a detergent composition and a cement additive comprising the anionic surfactant powder.

PRIOR ARTS

Anionic surfactants having a sulfuric acid group are used due to their emulsifying and dispersing abilities in wide fields ranging from domestic uses to industrial uses for detergents and additives for various chemical products, for example, detergents for clothes, kitchen detergents, dentifrice foaming agents, powder shampoos, emulsifier for emulsion polymerization, cement foaming agents and emulsifiers for medicines, cosmetics and the like.

Anionic surfactants represented by alkyl sulfates obtained by sulfurizing/neutralizing a higher alcohol are commercialized as powder products by drying solutions containing these surfactants. These alkyl sulfates generally have problems concerning stability in hard water and also give insufficient satisfaction in detergency. Therefore, it has been desired to improve these drawbacks.

On the other hand, a polyoxyalkylene alkyl ether sulfate obtained by adding an alkylene oxide to a higher alcohol and then sulfurizing and neutralizing the adduct has the characteristics that it has a lower krafft point, higher low-temperature solubility and has outstandingly higher stability in hard water than an alkyl sulfate having the same carbon number, and it is therefore used as a main base material of detergents and the like. However, it is very difficult to compound these sulfates in a large amount in a powder detergent composition because of the problems that these polyoxyalkylene alkyl ether sulfates have inherently deteriorated caking characteristics.

For example, a method of producing anionic surfactant granules is described in JP-A 5-331496. In Example 3 of the reference, a water slurry containing a polyoxyethylene alkyl ether sulfate in a solid content of 80% by weight is dried to obtain a granule. This granule has a water content as high as about 8% by weight and is not therefore said to be a granule which is improved in caking characteristics and has good fluidity.

That is why commercial products compounded of a large amount of a polyoxyalkylene alkyl ether are made to have a liquid or paste form; and nothing has been industrialized yet as a powder product having high fluidity.

DISCLOSURE OF INVENTION

It is an object of the present invention to provide an anionic surfactant powder comprising a polyoxyalkylene alkyl ether sulfate which powder has high stability in hard water and high low-temperature solubility and is improved in powder characteristics such as caking characteristics, and a method of producing the anionic surfactant powder.

The inventors of the present invention have found that an anionic surfactant powder comprising a polyoxyalkylene alkyl ether sulfate having a specified alkylene oxide average addition mol number has high stability in hard water, high low-temperature solubility and high fluidity while maintaining fundamental characteristics such as detergency.

Accordingly, the present invention provides an anionic surfactant powder comprising polyoxyalkylene alkyl ether sulfates in which the average addition mol number of alkylene oxides is 0.05 to 2, wherein the content of the polyoxyalkylene alkyl ether sulfates provided with alkylene oxides added thereto in an amount of 4 mol or more is 30% by weight or less based on the total anionic surfactant, an anionic surfactant powder further comprising a water-soluble inorganic salt, a method of producing each of these anionic surfactant powders, and a detergent composition and a cement additive comprising these anionic surfactant powders.

It is to be noted that in the present invention, the alkylene oxide average addition mol number means the alkylene oxide average addition mol number of a mixture of the alkyl sulfate and the polyoxyalkylene alkyl ether sulfate comprised in the anionic surfactant powders.

EMBODIMENTS OF INVENTION

In the polyoxyalkylene alkyl ether sulfate comprised in the powder of the present invention, the alkylene oxide average addition mol number is an important factor. The alkylene oxide average addition mol number is 0.05 to 2, preferably 0.1 to 1 and more preferably 0.2 to 0.8 with the view of obtaining superior powder characteristics and improving the caking characteristic when powdering the product of the present invention.

In the case where many compounds to which a large amount of alkylene oxides are added are present, the fluidity cannot be maintained even if the average addition mol number is within a range from 0.05 to 2. To state more concretely, it is necessary that the content of polyoxyalkylene alkyl ether sulfates to which 4 mol or more of alkylene oxides are added is 0 to 30% by weight, preferably 0 to 20% by weight and more preferably 0 to 15% by weight based on the whole anionic surfactant.

Also, differences in handling ability in the production and in performances are brought about also by a difference in the number of carbons of alkyl groups contained in the polyoxyalkylene alkyl ether sulfate. Namely, when the number of carbons becomes relatively small, the caking characteristics when the product is powdered is reduced, whereas when the number of carbons is excessively large, the performances such as the solubility of the powder are deteriorated. Therefore, the number of carbons of the alkyl group is preferably 8 to 20 and more preferably 10 to 18.

Examples of the polyoxyalkylene alkyl ether sulfate according to the present invention include compounds represented by the formula (I).

$$[R^1—O(AO)_n—SO_3]_pM \qquad (I)$$

wherein $R^1$ represents a straight-chain alkyl group having 8 to 20 carbon atoms, AO represents an oxyalkylene group or oxyalkylene groups having 2 to 4 carbon atoms, which may be the same as or different from one another, n represents the average addition mol number of alkylene oxides within a range from 0.05 to 2, M represents a cation and p represents the number of valence to M and n AO's may be the same as or different from one another.

In the formula (I), $R^1$ is preferably an alkyl group having 10 to 18 carbon atoms. AO is preferably an oxyalkylene group or oxyalkylene groups having 2 to 3 and particularly 2 carbon atoms. n is preferably 0.1 to 1 and particularly 0.2 to 0.8. M is preferably an alkali metal atom such as Na or K, an alkali earth metal atom such as Ca or Mg or an alkanol substituted or unsubstituted ammonium group and preferably an alkali metal atom and particularly Na. P is preferably 1 or 2 and more preferably 1.

No particular limitation is imposed on the distribution of alkylene oxides to be added to the polyoxyalkylene alkyl ether sulfate according to the present invention and an addition distribution, such as a broad distribution or a narrow distribution, obtained using a known method may be used. However, in the case of seeking both detergency and caking characteristics, it is preferable to comprise an alkyl sulfate to which no alkylene oxide is added in a fixed ratio. The content of the alkyl sulfate is preferably 30 to 95% by weight and more preferably 50 to 90% by weight in the polyoxyalkylene alkyl ether sulfate in which the average addition mol number of alkylene oxides is 0.05 to 2.

It is preferable that the anionic surfactant powder of the present invention further comprises a water-soluble inorganic salt. Examples of the water-soluble inorganic salt include sodium chloride, sodium sulfate, sodium carbonate and the like. Although no particular limitation is imposed on the content of the water-soluble inorganic salt in the anionic surfactant powder of the present invention as it is within the range in which the object of the present invention is not impaired, it is desired that the content is generally 10 parts by weight or less and preferably 2 parts by weight or less based on 100 parts by weight of the polyoxyalkylene alkyl ether sulfate for the purpose of keeping a high solid content of the polyoxyalkylene alkyl ether sulfate.

Also, the anionic surfactant powder of the present invention may comprise other additives as required. Examples of these other additives include alkalinizing agents such as silicates and carbonates, divalent metal ion-trapping agents such as citrates and zeolite, recontamination preventive agents such as polyvinyl pyrrolidone and carboxymethyl cellulose and others including caking preventive agents and antioxidants. These other additives may be used to the extent that the object of the present invention is not impaired.

The anionic surfactant powder of the present invention may also comprise water, an unreacted alcohol and the like. A preferable composition of the powder of the present invention comprises 60 to 80% by weight of the alkyl sulfate, 18 to 38% by weight of the polyoxyalkylene alkyl ether sulfate, 0.5 to 2.0% by weight of water, 0.5 to 2.0% by weight of the alcohol and polyoxyalkylene alkyl ether and 1.0 to 2.0% by weight of the inorganic salt.

The anionic surfactant powder of the present invention can be obtained by drying and granulating an aqueous solution or a paste comprising a polyoxyalkylene alkyl ether sulfate obtained by the following step 1 by using a known method shown in the step 2.

Step 1: Step of preparing an aqueous solution or a paste comprising a polyoxyalkylene alkyl ether sulfate.

Methods shown in the following (1) to (3) are exemplified to prepare the aqueous solution comprising the polyoxyalkylene alkyl ether sulfate.

(1) A method in which an alkylene oxide adduct of a higher alcohol obtained by adding alkylene oxides to an alcohol (hereinafter referred to as "higher alcohol") having 8 to 20 carbon atoms such that the average addition mol number of the alkylene oxides is 0.05 to 2 is sulfurized and neutralized.

(2) A method in which a higher alcohol is mixed with an alkylene oxide adduct of a higher alcohol such that the average addition mol number of the alkylene oxides in the mixture is 0.05 to 2, followed by sulfurizing and neutralizing.

(3) A method in which a higher alcohol and an alkylene oxide adduct of a higher alcohol which are separately sulfurized and neutralized in advance are mixed with each other such that the average addition mol number of the mixture is 0.05 to 2.

The sulfurization and the neutralization may be carried out using known methods. As a sulfurizing agent used for the sulfurization, sulfur trioxide or chlorosulfonic acid is preferable. When using sulfur trioxide gas, it is usually diluted with inert gas, such as, preferably dry air or nitrogen and used as a gas mixture in which the concentration of the sulfur trioxide gas is 1 to 8% by volume and preferably 1.5 to 5% by volume. Examples of the neutralizing agent include sodium hydroxide, potassium hydroxide, sodium carbonate and the like.

Unreacted materials comprised in the aqueous solution or paste of the polyoxyalkylene alkyl ether sulfate used in the present invention are factors deteriorating the purity and caking characteristics of the powder and are therefore undesirable. If the content of these unreacted materials is 5% by weight or less, this is allowable. It is preferable that the content be 2% by weight or less. Here, the unreacted materials imply unsulfurized alcohol and alkoxylate and further minute hydrocarbons and waxes which are by-produced in the reaction.

The content of the effective components of the neutralized product obtained by the above method is preferably 30% by weight or less. When the content exceeds 30% by weight, the viscosity increases and the handling characteristics are therefore impaired. Also, when the content of the effective components is 60 to 80% by weight, the product is put into a paste state, exhibiting fluidity. Therefore, the preparation of a paste having a relatively high content of the effective component during neutralization serves to decrease energy load during drying and is therefore preferable.

Also, in the present invention, a water-soluble inorganic salt may be present in the product. Typical examples of the water-soluble inorganic salt include sodium chloride, sodium sulfate, sodium carbonate and the like. Although each of these water-soluble inorganic salts may be added as it is, it may be by-produced by a reaction. For example, in the case of adding NaClO (sodium hypochlorite) to the aqueous solution or paste comprising the polyoxyalkylene alkyl ether sulfate for the purpose of improving a colar, NaCl (sodium chloride) is by-produced. Although there is a limitation to use, sodium chloride can be by-produced as an inorganic salt by adding sodium hypochlorite in this manner.

The obtained aqueous solution or paste comprising the polyoxyalkylene alkyl ether sulfate is subjected to the next step 2.

Step 2: Drying/granulating step

The step 2 is a step of drying/granulating the aqueous solution or paste comprising the polyoxyalkylene alkyl ether sulfate prepared in the step 1 in various conditions, wherein there is the case where the drying and granulating are carried out simultaneously.

As drying means, drying under vacuum is preferable to suppress a reduction in the qualities of the aqueous solution and paste comprising the polyoxyalkylene alkyl ether sulfate, namely to suppress, for example, hydrolysis caused by heating and the like. Further, in view of the foaming characteristics inherent to the polyoxyalkylene alkyl ether sulfate and cutting at the terminal of drying, a drying process using a continuous type or batch type vacuum dryer equipped with a stirring blade or a cutter or a drying process having the equivalent effect is preferable. Examples of the continuous dryer include rotary thin film evaporators such as Contro, Sebcon (trademarks, manufactured by Hitachi, Ltd.) and Sumith Thin Film Evaporator (manufactured by Shinko Panteck (Co., Ltd.)). In the case of these continuous dryers, the aqueous solution or paste of the polyoxyalkylene alkyl ether sulfate may be continuously fed into a rotary thin film evaporator at a reduced pressure to obtain a dried product. Also, examples of the batch type dryer include a mixer vacuum dryer (SV Mixer) manufactured by Shinko Pantech (Co., Ltd.), a microwave granulating dryer manufactured by Fukae Powtec (Co. Ltd.), a mixing dryer manufactured by Tanabe Wiltech (Co., Ltd.) and the like. Among these dryers, the microwave granulating dryer which is a batch type, enables the step 1 to be easily carried out in the same vessel and makes it possible to perform the drying and granulation of the step 2 is preferable because of reduced equipment burden.

As to the drying condition at this time, it is preferable to carry out drying under a vacuum at which the temperature of the aqueous solution or paste comprising the polyoxyalkylene alkyl ether sulfate is 80° C. or less from the viewpoint of decreasing thermal hysteresis and suppressing a reduction in qualities such as decomposition.

More specific examples of the drying method include methods of drying the aqueous solution or paste comprising the polyoxyalkylene alkyl ether sulfate obtained in the step 1 according to any of following methods (4) to (6).

(4) A method in which an aqueous solution or a paste comprising a polyoxyalkylene alkyl ether sulfate or a mixture of an aqueous solution or a paste comprising a polyoxyalkylene alkyl ether sulfate with an aqueous solution, a paste or a powder comprising an alkyl sulfate is dosed altogether into a batch type vacuum drier equipped with a stirring blade(s) and/or a cutter and dried at a reduced pressure.

(5) A method in which an anionic surfactant powder is placed in a batch type vacuum drier equipped with a stirring blade and/or a cutter in advance to the extent that a stirring or cutting effect is obtained and then the powder is dried at a reduced pressure with supplying an aqueous solution or a paste comprising a polyoxyalkylene alkyl ether sulfate at such a feed rate that the powder in the drier keeps a powder state. As the anionic surfactant powder placed in advance at this time, only the anionic surfactant powder obtained in the present invention, a combination of the anionic surfactant powder with an alkyl sulfate powder or only an alkyl sulfate powder may be used.

(6) A method in which an aqueous solution or a paste comprising a polyoxyalkylene alkyl ether sulfate is dried, while feeding it continuously into a rotary thin film evaporator, at a reduced pressure.

On the other hand, in the case of an aqueous solution comprising 30% by weight or less of the polyoxyalkylene alkyl ether sulfate, it is relatively less viscous and therefore has fluidity, so that a dryer using a spray dryer or the like may be used. However, in the case of an aqueous solution comprising the polyoxyalkylene alkyl ether sulfate in an amount of 30% by weight or more and 60% by weight or less, the viscosity is significantly increased, causing clogging and the like in a spraying apparatus and therefore such a consentlation is undesirable.

The anionic surfactant powder in the present invention may be granulated as required when used. No particular limitation is imposed on a granulator which can be used at this time and for example, a stirring rolling granulator (manufactured by Fukae Powtec (Co., Ltd.), Tanabe Wiltech (Co., Ltd.) or the like) or the like may be used. The anionic surfactant powder may be granulated by adding water, an aqueous solution comprising a polyoxyalkylene alkyl ether sulfate or the like as a binder and a granulated product having a proper particle size may be obtained by screening. Although there is no particular limitation to the size and shape of the granulated product at this time, the particle diameter is preferably 125 to 3000 μm and more preferably 125 to 2000 μm to improve solubility in water. Also, the particle diameter is preferably 125 μm or more and more preferably 500 μm or more to prevent a rise of powder dust during handling. Therefore, the particle diameter is particularly preferable in a range from 500 to 2000 μm.

Also, extrusion granulation may be carried out. No particular limitation is imposed on a kneader which may be used at this time and an extrusion granulator (manufactured by, for example, (Corporation) Dalton and the like) and the like may be used. Using the same binder as above, the anionic surfactant powder may be granulated. Although there is no particular limitation to the size of the extrusion granulated product, a granulated product having a diameter of 0.5 to 1.0 mm and a length of 3 to 5 mm is preferable from the view point of the handling.

Furthermore, granulation consisting of a combination of extrusion granulation and cutting granulation or a combination of extrusion granulation, cutting granulation and stirring rolling granulation may be carried out. Specifically, a granulated product of an anionic surfactant powder may be obtained using, for example, a method in which the cylindrical granulated product obtained by an extrusion granulator is subjected to screening after cut by a cutting granulator to obtain a granulated product having a specified particle diameter or a method in which the cylindrical granulated product obtained by using an extrusion granulator is placed in a stirring rolling granulator after cut by a cutting granulator and is further granulated by adding a fixed amount of water, followed by screening to obtain a granulated product having a specified particle diameter.

The granulated product of the anionic surfactant powder obtained by each of these methods is preferably improved in powder properties by coating the surface thereof with an inorganic powder such as sodium sulfate or zeolite or an alkyl sulfate powder as required.

The anionic surfactant powder of the present invention is added to and mixed with other detergent raw materials to constitute a detergent composition, which is then made into a preparation, whereby a detergent having high stability in hard water, good foaming ability even in hard water and high low-temperature solubility can be obtained and the anionic surfactant powder is therefore very useful as a detergent base material.

In the present invention, as the surfactants among the detergent raw materials, other anionic surfactants, nonionic surfactants and further, as required, cationic surfactants and amphoteric surfactants besides the anionic surfactant powder used in the present invention may be used. Examples of the other anionic surfactants include alkylbenzene sulfonates, alkyl or alkenyl ether sulfates, alkyl or alkenyl sulfates, α-olefin sulfonates, α-sulfo fatty acid salts or esters, alkyl or alkenyl ether carboxylates, fatty acid salts and the like. As the counter ion of the anionic surfactant, alkali metal ions are preferable from the viewpoint of improving detergency. The content of the anionic surfactant, including the anionic surfactant powder used in the present invention in the detergent composition of the present invention, is preferably 1 to 50% by weight and more preferably 5 to 30% by weight from the viewpoint of detergency.

Examples of the nonionic surfactant include polyoxyalkylene alkyl ethers, polyoxyalkylene alkylphenyl ethers, polyoxyalkylene fatty acid esters, polyoxyethylenepolyoxypropylene alkyl ethers, polyoxyalkylenealkylamines, glycerol fatty acid esters, higher fatty acid alkanolamides, alkyl glycosides, alkylglucoseamides, alkylamine oxides and the like. Ethylene oxide adducts of alcohols having 10 to 18 and preferably 12 to 14 carbon atoms or a mixture of ethylene oxide and propylene oxide adducts, namely, polyoxyalkylene alkyl ether having an alkylene oxide average addition mol number of 5 to 30 and preferably 6 to 15 are preferable in view of detergency. Also, polyoxyethylenepolyoxypropylene alkyl ethers are preferable in view of detergency and solubility. The compounds may be obtained by reacting propylene oxide and further ethylene oxide with an ethylene oxide adduct of an alcohol having 10 to 18 and preferably 12 to 14 carbon atoms. The content of the nonionic surfactant in the detergent composition of the present invention is preferably 1 to 50% by weight and more preferably 5 to 30% by weight from the viewpoint of detergency.

Examples of the cationic surfactant include alkyltrimethylammonium salts and the like and examples of the amphoteric surfactants include carbobetaine type or sulfobetaine type surfactants.

The total content of the surfactant in the detergent composition of the present invention is preferably 10 to 60% by weight, more preferably 20 to 50% by weight and particularly preferably 27 to 45% by weight from the viewpoint of detergency and of obtaining desired powder properties of the detergent composition.

Also, the detergent composition of the present invention may be compounded of water-soluble inorganic salts such as carbonates, hydrogen carbonates, silicates, sulfates, sulfites or phosphates from the viewpoint of improving the ionic strength in a washing liquid. Here, the amount of the carbonate to be compounded in the detergent composition is preferably 25% by weight or less, more preferably 5 to 20% by weight and particularly preferably 7 to 15% by weight as converted into an anhydride from the viewpoint of detergency and low-temperature dispersibility in the condition that the composition is allowed to stand for a long time in cool water. Also, the sum of the carbonate and the sulfate in the detergent composition is preferably 5 to 35% by weight, more preferably 10 to 30% by weight and particularly preferably 12 to 25% by weight as converted into an anhydride.

Moreover, the detergent composition of the present invention may be compounded of an alkali metal silicate. As the alkali metal silicate, any of crystal types and amorphous types may be used. However, a crystal type is preferably comprised because it has cation-exchange ability. In the alkali metal silicates, the ratio of $SiO_2/M^1{}_2O$ ($M^1$ represents an alkali metal) is preferably 2.6 or less, more preferably 2.4 or less and particularly preferably 2.2 or less from the viewpoint of alkalinizing ability. Also, the ratio is preferably 0.5 or more, more preferably 1.0 or more, more preferably 1.5 or more, particularly preferably 1.7 or more from the viewpoint of storage stability. Here, examples of the amorphous alkali metal silicate include Britesil C20, Britesil $H_2O$, Britesil C24 and Britesil H24 (trademarks, manufactured by The PQ Corporation) which are, for example, granules of JIS No. 1 or No. 2 sodium silicates or dried products of water glass. Also, NABION 15 (trademark, manufactured by RHONE-BOULENC) which is a complex of sodium carbonate and an amorphous alkali metal silicate may be used.

Alkali metal silicates when crystallized have high alkalinizing ability and cation-exchange ability equal to that of A4 type zeolite and are very preferable base materials also from the viewpoint of low-temperature dispersibility. For this, the detergent composition of the present invention preferably comprises one or more crystalline alkali metal silicates selected from compounds represented by the following formulae (II) or (III).

$$X(M^2{}_2O).y(SiO_2).z(M^3{}_uO_v).w(H_2O) \quad (II)$$

wherein $M^2$ represents an Ia group element (preferably K and/or Na) in the periodic table, $M^3$ represents one or more types (preferably Mg and Ca) selected from IIa group elements, IIb group elements, IIIa group elements, IVa group elements and VIII group elements in the periodic table, y/x=0.5 to 2.6, z/x=0.001 to 1.0, w=0 to 20 and v/u=0.5 to 2.0.

$$M^2{}_2O.x'(SiO_2).y'(H_2O) \quad (III)$$

wherein $M^2$ represents the same meaning as the above, x'=1.5 to 2.6 and y'=0 to 20 (preferably substantially 0).

These crystalline alkali metal silicates are comprised in the detergent composition of the present invention in an amount of preferably 0.5 to 40% by weight, more preferably 1 to 25% by weight, particularly preferably 3 to 20% by weight and most preferably 5 to 15% by weight. Here, the amount of crystalline silicates are preferably 20% by weight or more, more preferably 30% by weight or more and particularly 40% by weight or more based on the total amount of the alkali metal silicates. This crystalline alkali metal silicate is commercially available, for example, under the trade name of "Prifeed" (δ—$Na_2O.2SiO_2$) from Tokuyama Siltech. Those having a powder form and/or a granular form may be used. Particularly, the metal silicate is preferably used in combination with sodium carbonate.

Also, the detergent composition of the present invention may be compounded of an organic acid salt such as a citrate, hydroxyiminodisuccinate, methylglycine diacetate, glutamic acid diacetate, asparagine diacetate, cerin diacetate, ethylenediamine disuccinate and ethylenediamine tetraacetate from the viewpoint of improving metal ion sequestrating ability. Also, it is preferable to compound a cation-exchange type polymer having a carboxylic acid group and/or a sulfonic acid group from the viewpoint of improving metal ion sequestrating ability and the ability of dispersing soils of solid particles. Particularly, an acrylic acid/maleic acid copolymer salt having a molecular weight of 1000 to 80000, polyacylate or polyacetal carboxylate such as polyglyoxylic acid having a molecular weight of 800 to 1000000 and preferably 5000 to 200000 as described in the publication of JP-A No. 54-52196 are preferable. The cation-exchange type polymer and/or the organic acid salt are preferably compounded in the detergent composition in an amount of preferably 0.5 to 12% by weight, more preferably 1 to 10% by weight, still more preferably 1 to 7% by weight and particularly preferably 2 to 5% by weight in view of detergency.

Also, the detergent composition of the present invention may be compounded of a crystalline aluminosilicate such as A-type, X-type and P-type zeolite. The average primary particle diameter of the crystalline aluminosilicate is preferably 0.1 to 10 μm. Also, an amorphous aluminosilicate may be compounded which has an oil absorbing ability of 80 mL/100 g or more which is measured according to JIS K 5101 method. Examples of the amorphous aluminosilicate include those described in each publication of JP-A Nos. 62-191417 and 62-191419. It is preferable to compound the amorphous aluminosilicate in the detergent composition of the present invention in an amount of 0.1 to 20% by weight.

The detergent composition of the present invention may be compounded of a dispersant or a color-transfer preventive agent such as carboxylmethyl cellulose, polyethylene glycol, polyvinyl pyrrolidone and polyvinyl alcohol, bleaching agent such as a percarbonate, bleaching activator, enzymes, biphenyl type or stilbene type fluorescent dyes, antifoaming agent, antioxidant, blueing agent, perfumes and the like. It is to be noted that a group of the granulated particles such as enzymes, a bleaching activator and an antifoaming agent which are separately granulated may be after-blended.

Examples of the bleaching activator to be used in the present invention include tetraacetylethylenediamine, glucose pentaacetate, tetraacetyl glycol uril and compounds represented by the formula (I), (II), (III) or (IV) in JP-A No. 8-3593 (e.g., sodium p-phenol sulfonates (e.g., sodium acetoxybenzenesulfonate, sodium benzoyloxybenzene-sulfonate and linear or branched octanoyl/nonanoyl/decanoyl/dodecanoylphenol sulfonate) or p-hydroxybenzoates (e.g., acetoxybenzenecarboxylic acid, octanoyloxybenzenecarboxylic acid, decanoyloxybenzenecarboxylic acid and dodecanoyloxybenzenecarboxylic acid)).

No particular limitation is imposed on the enzymes to be used in the present invention. Examples of the enzyme include hydrolases, oxidoreductases, lyases, transferases and isomelases. Particularly preferable examples of the enzymes include cellulase, protease, lipase, amylase, prulanase, esterase, hemicellulase, peroxidase, phenol oxidase, protopectinase and pectinase. These enzymes may be used in combinations of two or more. A combination of protease and cellulase is particularly preferable in consideration of the dispersibility of colorants when these enzymes are granulated and the prevention of dyeing clothes. Although this reason is not clarified, it is predicted that the effect of cellulase on the removal of cortexes inside of fibers is improved in cooperation with the effect of protease on the removal of stains and keratin stuck to the surface of fibers, which makes it possible to prevent the dye from remaining on sebum components.

The foregoing enzymes may be produced using any method without any particular limitation. Generally, those obtained by filtering a cultured product comprising enzymes produced by microorganisms and further drying are used. Also, the enzymes may comprise stabilizers, sugars, inorganic salts such as sodium sulfate, polyethylene glycol, impurities and water depending on culture conditions and separating conditions.

Methods of adding these base materials in a production step are as follows. As to sodium carbonate, there is a method in which it is compounded in an aqueous slurry, which is then subjected to spray-drying to make a powder, a method in which sodium carbonate whose average particle diameter is adjusted to about 1 to 40 μm is added in a granulating step or in a surface reforming step and a method in which dense ash or light ash is after-blended. Examples of a method of adding the amorphous alkali metal silicate include a method in which it is compounded in an aqueous slurry, which is then subjected to spray-drying and a method in which a granulated one is after-blended. As to the crystalline alkali metal silicate, there is a method in which the average particle diameter thereof is adjusted to about 1 to 40 μm, preferably about 1 to 30 μm, more preferably about 1 to 20 μm and still more preferably about 1 to 10 μm and the adjusted alkali metal silicate is added, for example, in a granulating step or in a surface reforming step. At this time, it is preferable to mix a base material such as a crystalline and/or amorphous aluminosilicate from the viewpoint of storage stability. Also, there is a method in which granules prepared by a method using a roller compactor or the like as described in the publication of JP-A No. 3-16442 are after-blended and the like.

Also, in another preferred embodiment, the detergent composition of the present invention may be compounded of an anionic surfactant having a sulfonic group in an amount of 5% by weight or more based on the detergent composition. The use of the anionic surfactant makes it possible to keep better dispersibility among detergent particles in the condition that the detergent is allowed to stand in cool water for a long time.

The anionic surfactant having a sulfonic acid group is compounded in the detergent composition of the present invention in an amount of preferably 5% by weight more, more preferably 7% by weight or more and particularly preferably 10% by weight or more. Preferable examples of the anionic surfactant having a sulfonic acid group include alkylbenzene sulfonates, α-olefin sulfonates, α-sulfo-fatty acid salts or their esters. Alkylbenzene sulfonates are particularly preferable.

No particular limitation is imposed on a method of producing the detergent composition of the present invention and on the shape of the detergent composition, and the anionic surfactant powder of the present invention and other detergent raw materials may be dry-blended simply using a V-type blender or a Nauta Mixer (manufactured by Hosokawa Micron (Corporation)) or the like or granulated.

In the case of granulating, a binder may be compounded as required. As the binder, an aqueous solution or a paste comprising the aforementioned various surfactants may be used. Other than the above, a cation exchange type polymer having a carboxylic acid group and/or a sulfonic acid group which have (has) ion sequestrating ability and the ability of dispersing soils of solid particles or a high-molecular compound such as polyethylene glycol may be used as effective binders. There is no particular limitation to a granulating method and (1) a stirring rolling granulating method, (2) a fluidized bed granulating method, (3) an extrusion granulating method or (4) a compression granulating method such as tabletting (making tablet), briquetting and compacting is used to make desired granules of a detergent composition.

Next, each granulating method will be explained in detail.

(1) Stirring Rolling Granulating Method

The stirring rolling granulating method is a method in which a liquid or solid binder is added to the detergent composition comprising the anionic surfactant powder of the present invention which is placed in a vessel and the mixture is granulated with heating or cooling as the case may be and with rotating a stirring blade as required to carry out granulation. According to this method, the solubility of the resulting granule can be controlled by appropriately controlling the type and amount of the binder to be added or granulating time. The granulation may be carried out either in a batch system or in a continuous system. Also, the binder may be added either in a lump sum or under the control of addition time or intermittently to make a desired granule or according to the qualities of the binder. When the binder is added in a liquid state, it is preferably added in a spray system. The aqueous solution or paste of the surfactant is preferably used as the binder. Its amount may be properly controlled such that the total content of the surfactants in the detergent composition is preferably 10 to 60% by weight, more preferably 20 to 50% by weight and particularly preferably 27 to 45% by weight.

Examples of a granulator which may be used include, though not particularly limited to, (1) mixers of the type provided with a mixing vessel having a stirring shaft, to which a stirring blade is set to mix powders; for example, Henshel Mixer (manufactured by Mitsui Miike Kakoki (Corporation)), High Speed Mixer (manufactured by Fukae Powtec (Co., Ltd.)), Vertical Granulator (manufactured by (Corporation) Powrex), Redige Mixer (manufactured by Matsubo (Corporation)), Proshear Mixer (manufactured by Pacific Machinery and Engineering (Co., Ltd.)) and the like, (2) mixers of the type carrying out mixing by rotating a ribbon-like blade forming a spiral in a fixed container having a cylindrical or semi-cylindrical form; for example, Ribbon Mixer (manufactured by Nichiwa Kikai Kogyo (Corporation), Batch Kneader (manufactured by Satake Chemical Equipment (Mtf., Ltd.)) and the like and (3) mixers of the type carrying out mixing by making a screw revolve on an axis parallel to the wall of a conical container along the container; for example, Nauta Mixer (manufactured by Hosokawa Micron (Corporation)).

In this method, granules having an average particle diameter of about 70 to 5000 μm can be obtained and drying, coating and classification can be carried out after granulating.

(2) Fluidized Bed Granulating Method

The fluidized bed method is a method in which the detergent composition comprising the anionic surfactant powder of the present invention is kept in a fluidized state by a fluid introduced from the under part of an apparatus and a liquid binder is added to this fluidized bed to carry out coagulation granulating. When using a plasticized thermoplastic material such as molten polyethylene glycol, granulation is carried out while decreasing the plasticity by normal-temperature or cool air. A relatively porous granule of a detergent composition having an average particle diameter of about 100 to 2000 μm and high solubility can be obtained. In the case of introducing hot air, the temperature of the air is preferably designed to be 80° C. or less from the viewpoint of suppressing a reduction in qualities caused by the decomposition of the polyoxyalkylene alkyl ether sulfate. In order to obtain an even granule, the binder is preferably added in a spray system. There is no particular limitation to the amount of the binder to be added and the amount may be optionally controlled as aforementioned. Preferable examples of a fluidized bed granulator include a Flow Coater (manufactured by Freund Industrial (Co., Ltd.)), Spiler Flow (manufactured by the same company), Aglomaster (manufactured by Hosokawa Micron (Corporation)), Glowmax (manufactured by Fuji Paudal (Co., Ltd.)) and the like. After granulating, coating and classification may be optionally carried out.

(3) Extrusion Granulating Method

In the extrusion granulating method, the aforementioned binder is added to the detergent composition comprising the anionic surfactant powder of the present invention. The mixture is kneaded to provide plasticity and then pressed to a die or a screen plane having a large number of holes to extrude the mixture from these holes, thereby carrying out molding. A granule having an even particle size and an average particle diameter of 0.3 to 30 mm is obtained. In the case of using a thermoplastic material as the binder, it is heated and extrusion-molded in the condition under which the binder exhibits thermoplasticity. It is preferable to premix the binder in advance by using a Nauta Mixer or the like. Also, the granules obtained by the aforementioned stirring rolling granulating method or fluidized bed granulating method may be further extrusion-granulated. No particular limitation is imposed on the amount of the binder to be added and the amount can be optionally controlled as aforementioned. Preferable examples of the extrusion granulator include Pelletor Double (manufactured by Fuji Paudal (Co., Ltd.)), Twin Domegran (manufactured by the same company) and the like. Cutting, granulation (rounding) and classification are carried out appropriately as aftertreatment after granulating, and also, the particle size may be controlled.

(4) Tabletting (Making Tablet)/Briquetting/Compacting

The tabletting (making tablet)/briquetting/compacting are all compression granulating methods, which are preferable in the case of preparing a granule of a detergent composition in which dust is hardly produced and each of particle size is uniform. The tabletting is a granulating method in which the detergent composition comprising the anionic surfactant powder of the present invention is filled in a mold and then pressed by a mallet. Also, among roll press methods in which the detergent composition comprising the anionic surfactant powder of the present invention is compressed and molded between two rotating rolls, a method using a pattern engraved on the surface of the rolls is called briquetting and a method using no engraved pattern is called compacting. In these compression granulating methods, a compression force of as high as 0.2 to 5 ton/cm$^2$ is applied to the detergent composition to granulate and a problem concerning the solubility therefore arises. In this case, the solubility can be improved by adding a rupture agent such as cellulose and magnesium sulfate. In the tabletting, a granule having a diameter of about 0.5 to 50 mm can be obtained. Also, flakes obtained by molding by the compacting are cut, whereby a compacted granule of 1 to 2 mm or less in size can be made. Examples of the shape of the pattern formed on the surface of the rolls of a briquetting apparatus include a pillow type, lens type, almond type, prism type, wave type and the like, among which an optional one may be selected and used.

Also, the anionic surfactant powder of the present invention can be appropriately used as a cement additive, particularly as an air entraining agent. The anionic surfactant powder at this time is added together with cement and aggregates and these compounds are mixed with water to obtain concrete and mortar in which independent fine air cells having a diameter of about 0.25 to 0.025 mm are uniformly dispersed. These concrete and mortar involving fine air cells have many advantages, for example, in being improved in durability against freezing and thawing and in being improved in workability. When the anionic surfactant powder of the present invention is used, air cells formed are highly stable and therefore concrete and mortar which are reduced in cracks after they are applied are obtained. There is no particular limitation to the shape of these cement and mortar and a powder form, granular form or the like may be adopted. It is preferable that the anionic surfactant powder be prepared and used as a composition by mixing it in a dry system together with components comprised in usual cement such as cement, calcium oxide, calcium hydroxide and calcium sulfate and with powders which give no adverse effect after applied when it is used.

EXAMPLES

All designations of % in examples indicate weight percentage, unless otherwise noted.

Synthetic Example 1

A falling thin film reactor having an inside diameter of 14 mmφ and a length of 4 m was continuously charged with 2.0% by volume of sulfur trioxide gas together with a higher alcohol (molecular weight: 199) provided with alkyl groups having 12 to 16 carbon atoms wherein the distribution of $C_{12}/C_{14}/C_{16}$=67%/28%/5% at 60° C. to react. The flow rate was controlled such that the reaction molar ratio of the sulfur trioxide gas to the higher alcohol was 1.01. The resulting sulfate was neutralized by 32.2% aqueous sodium hydroxide and 75% phosphoric acid (buffer solution) was added to the sulfate and exactly adjusted to pH 10 by adding 32.1% aqueous sodium hydroxide solution. The effective component of the resulting sodium alkylsulfate paste was 73%.

Synthetic Example 2

The same reaction as in Synthetic Example 1 was run except that an ethoxylate, having the average molecular weight of 242, obtained by adding ethylene oxide in an amount of 1.0 mol in average to a higher alcohol, provided with alkyl groups having 12 to 16 carbon atoms wherein the distribution of $C_{12}/C_{14}/C_{16}$=67%/28%/5%, by using a potassium hydroxide catalyst, was used in place of the higher alcohol and 4.0% aqueous solution of sodium hydroxide was used. The effective component of the resulting aqueous sodium polyoxyethylenealkylsulfate solution was 25.4%.

Synthetic Example 3

The same reaction as in Synthetic Example 1 was run except that an ethoxylate, having the average molecular weight of 280, obtained by adding ethylene oxide in an amount of 2.0 mol in average to a higher alcohol, provided with alkyl groups having 12 and 14 carbon atoms wherein the distribution of $C_{12}/C_{14}$=75%/25%, by using a Kyoward 2030 catalyst (manufactured by Kyowa Chemical Industry Co., Ltd.) was used in place of the higher alcohol and 3.6% aqueous solution of sodium hydroxide was used. The effective component of the resulting aqueous sodium polyoxyethylenealkylsulfate solution having a narrow distribution (the width of the distribution of addition mol numbers is narrow) was 25.2%.

Synthetic Example 4

The same reaction as in Synthetic Example 1 was run except that an ethoxylate, having the average molecular weight of 280, obtained by adding ethylene oxide in an amount of 2.0 mol in average to a higher alcohol, provided with alkyl groups having 12 and 14 carbon atoms wherein the distribution of $C_{12}/C_{14}$=75%/25%, by using an alkylene oxide addition reaction catalyst synthesized using the method described in Example 1 of JP-A No. 2001-327866 was used in place of the higher alcohol and 3.6% aqueous solution of sodium hydroxide was used. The effective component of the resulting aqueous sodium polyoxyethylenealkylsulfate solution having a narrow distribution was 25.1%.

Synthetic Example 5

The same reaction as in Synthetic Example 1 was run except that a raw material, having the average molecular weight of 209, prepared by compounding a higher alcohol, provided with alkyl groups having 12 to 16 carbon atoms wherein the distribution of $C_{12}/C_{14}/C_{16}$=67%/28%/5%, with an ethoxylate obtained by adding ethylene oxide in an amount of 1.0 mol in average to the same higher alcohol by using a potassium hydroxide catalyst in a ratio of 75%:25% was used in place of the higher alcohol and 30.1% aqueous solution of sodium hydroxide was used. The effective component of the resulting sodium polyoxyethylenealkylsulfate paste was 72%.

Synthetic Example 6

The same reaction as in Synthetic Example 1 was run except that an ethoxylate, having the average molecular weight of 242, obtained by adding ethylene oxide in an amount of 1.0 mol in average to a higher alcohol, provided with alkyl groups having 12 to 16 carbon atoms wherein the distribution of $C_{12}/C_{14}/C_{16}$=67%/28%/5%, by using a potassium hydroxide catalyst was used in place of the higher alcohol and 28.9% aqueous solution of sodium hydroxide was used. The effective component of the resulting sodium polyoxyethylenealkylsulfate paste was 73%.

Example 1

A microwave dryer (manufactured by Fukae Powtec (Co., Ltd.), FMD-65JE Model) having a capacity of 65 L was charged with 9.36 kg of a mixed solution obtained by mixing the paste comprising the sodium alkyl sulfate (AS) obtained in Synthetic Example 1 with the aqueous solution comprising the sodium polyoxyethylenealkylsulfate (ES) obtained in Synthetic Example 2 such that the ratio by weight of the effective components, namely AS:ES was 85:15. The mixture was dried and powdered under the condition that jacket temperature was 50 to 60° C., pressure was 9.3 kPa, the revolution of the agitator was 200 r/min and the revolution of the chopper was 2000 r/min, to obtain an anionic surfactant powder comprising a sodium polyoxyethylenealkylsulfate (average molecular weight:310) having an ethylene oxide average addition mol number of 0.25.

Examples 2 to 11

Anionic surfactant powders comprising sodium polyoxyethylene alkylsulfates having the ethylene oxide average addition mol numbers shown in Table 1 were obtained in the same manner as in Example 1 except that mixed solutions were used which were obtained by mixing pastes comprising sodium alkylsulfate (AS) having the alkyl compositions shown in Table 1 with aqueous solutions comprising sodium polyoxyethylenealkylsulfate (ES) which had the alkyl compositions shown in Table 1 and to which ethylene oxide was added in an amount of 1.0 mol in average such that the ratio by weight of the effective components was the ratios shown in Table 1.

Comparative Examples 1 and 2

Anionic surfactant powders comprising sodium alkylsulfates were obtained in the same manner as in Example 1 except that pastes containing sodium alkylsulfates (AS) having the alkyl composition shown in Table 1.

Test Example 1

A part of each of the anionic surfactant powders obtained in Examples 1 to 11 and Comparative Examples 1 and 2 was granulated in the same apparatus and then screened to obtain samples having a particle diameter of 500 μm or more and less than 1410 μm. The caking characteristics, stability in hard water and detergency of these samples were evaluated according to the following method. These results are shown in Table 1.

<Caking Characteristics>

The caking characteristics of each sample were evaluated according to the following standard.

⊚: The occurrence of caking was not observed after one month.

○: The occurrence of caking was observed a little after two weeks.

χ: The occurrence of caking was observed just after the test was started.

<Stability in Hard Water>

The test was conducted according to the synthetic detergent test method (JIS K3362). 100 mL of hardwater (16° DH) was added with stirring to 100 mL of a test solution having a concentration of 2.0 g/L as converted into an anhydride with regard to each of Examples 1 to 3 and Comparative Example 1 and to 100 mL of a test solution having a concentration of 3.0 g/L as converted into an anhydride with regard to each of Examples 4 to 11 and Comparative Example 2 with stirring. Each resulting solution was allowed to stand in a thermostatic chamber kept at 50° C. for 10 minutes and then taken out to rate as follows: the case where a crosswise character on the evaluating plate was observed was rated as "Pass" and the other cases were rated as "Failure".

<Detergency (Foaming Ability and Foam Stability)>

This test was conducted according to the synthetic detergent test method (JIS K3362). Each sample was dissolved in hard water (16° DH) in a concentration of 2.0 g/L as converted into an anhydride to prepare a test solution. The height (mm) of foams produced when 200 mL of the test solution was made to fall down on the surface of a liquid (50 mL of the same test solution) from an aptitude of 900 mm above the liquid level in the condition of a temperature of 40° C. over 30 seconds was measured after 1 minute as the foaming ability. The height (mm) of the foam obtained after 5 minutes was measured as the foam stability. These measurements were carried out three times each to find each average, which was shown as a relative value when the value of Comparative Example 2 was regarded as 1.

| <Detergent composition> | |
|---|---|
| Anionic surfactant powder | 10% |
| Nonionic surfactant (Emulgen 120, manufactured by Kao Corporation) | 5% |
| Soap (sodium salt of Lunac P-95 (manufactured by Kao Corporation) | 2% |
| 4A type zeolite | 30% |
| Soda ash | 15% |
| No. 1 water glass | 5% |
| Sodium sulfate | 16% |
| Acrylic acid/maleic acid copolymer (Socaran CP-5, manufactured by BASF) | 3% |
| Sodium percabonate | 10% |
| TAED | 4% |

<Method of Evaluation of Detergency>

The detergency was evaluated by the following procedures.

(1) Commercially available soiled cloth (wfk 10D, reflectance of the cloth before soiled=80.1%) was cut into a size of 3×3 cm to measure the reflectance of the cloth before washed

TABLE 1

| | Alkyl composition(%) | | | | AS:ES weight ratio | Ethyleneoxide average addition mol number | Ratio of adducts having an ethylene oxide addition mol number of 4 or more (%) | Result of evaluation of performance | | | |
|---|---|---|---|---|---|---|---|---|---|---|---|
| | C12 | C14 | C16 | C18 | | | | Caking characteristics | Stability in hard water | Foaming ability | Foam stability |
| Example 1 | 67 | 28 | 5 | — | 85:15 | 0.25 | 3.3 | ◎ | pass | 11.5 | 1.21 |
| Example 2 | | | | | 70:30 | 0.5 | 6.6 | ○~◎ | pass | 12.5 | 1.23 |
| Example 3 | | | | | 40:60 | 1.0 | 13.2 | ○ | pass | 13.5 | 1.27 |
| Comparative Example 1 | | | | | 100:0 | 0 | 0 | ◎ | failed | 9.5 | 1.13 |
| Example 4 | 55 | 25 | 10 | 10 | 85:15 | 0.25 | 3.2 | ◎ | pass | 9.2 | 1.17 |
| Example 5 | | | | | 70:30 | 0.5 | 6.4 | ○~◎ | pass | 10.0 | 1.18 |
| Example 6 | | | | | 40:60 | 1.0 | 12.9 | ○ | pass | 10.8 | 1.22 |
| Example 7 | 50 | — | 24 | 26 | 85:15 | 0.25 | 3.1 | ◎ | pass | 1.4 | 1.11 |
| Example 8 | | | | | 70:30 | 0.5 | 6.2 | ○~◎ | pass | 1.6 | 1.22 |
| Example 9 | — | 50 | 24 | 26 | 85:15 | 0.25 | 3.0 | ◎ | pass | 1.3 | 1.11 |
| Example 10 | | | | | 70:30 | 0.5 | 6.0 | ◎ | pass | 1.5 | 1.22 |
| Comparative Example 2 | | | | | 100:0 | 0 | 0 | ◎ | failed | 1 | 1 |
| Example 11 | — | — | — | 100 | 40:60 | 1.0 | 10.7 | ◎ | pass | — | — |

As is clear from the results shown in Table 1, the products of the present invention satisfy the stability in hard water and detergency to be required and have good caking characteristics and, namely, is a powder suitable to excellent fabric detergents which also satisfy the storage stability.

Test Example 2

Using the anionic surfactant powder obtained in Example 10, detergent compositions having the following percentage compositions were prepared and the detergency of each composition was evaluated according to the following methods. Also, for comparison, using a commercially available sodium alkylsulfate powder (trademark: Emal 10P-HD, manufactured by Kao Indonesia Chemicals (Corporation)) as the anionic surfactant powder, a detergent composition was prepared in the same manner as the above to evaluate its detergency. The results are shown in Table 2.

(measuring device: Nippon Denshoku 300A, 5 pieces×2 (front and back) per one specimen).

(2) The above detergent composition was divided into 4 groups, specifically, (a) the anionic surfactant powder, (b) the nonionic surfactant, soap, 4A type zeolite, soda ash, No. 1 water glass, sodium sulfate and acrylic acid/maleic acid copolymer, (c) Sodium percarbonate and (d) TAED, which were then dissolved in 30° C. ion exchange water in a concentration (=80 g/L) 10 times the concentration of a detergent solution (concentration of the detergent composition: 8 g/L) to prepare 4 types of mother liquor.

(3) Hard water having a hardness of 16° DH was prepared and set to 30° C.

(4) A test tube, Launder-O-Meter of Suga Test Instruments Co., Ltd., having a volume of about 250 ml, LM-16 Model) was charged with 32 Teflon balls and 40 mL of 30° C. ion exchange water, to which were then added 8 mL of the hard water prepared in (3) and the four types of mother liquor produced in (2) and then 5 soiled clothes were fed into the test tube, which was then set to the apparatus.

(5) The clothes were washed at 30° C. for 30 minutes.

(6) After washed, the soiled clothes were taken out, rinsed with city water, then dewatered and dried.

(7) The reflectance of each cloth after washed was measured (measuring device: Nippon Denshoku 300A), and the washing rate is calculated from the reflectances measured before and after washing according to the following formula to calculate an average of the obtained washing rates.

Washing rate (%)=(reflectance after washing−reflectance before washing)/(reflectance of cloth before soiled−reflectance before washing)×100

TABLE 2

| | Reflectance(%) | | Washing |
|---|---|---|---|
| | Before washing | After washing | rate (%) |
| Example 10 | 46.1 | 65.3 | 56.5 |
| Comparative Product | 46.7 | 63.5 | 50.3 |

As is clear from the results of Table 2, it is found that the anionic surfactant powder of the present invention is superior to the commercially available anionic surfactant powder in detergency when compounded in a detergent.

Test Example 3

Using the anionic surfactant powders obtained in Example 1, Comparative Example 1, Example 10 and Comparative Example 2, detergent compositions having the same composition as the detergent composition of Test Example 2 were prepared and the detergency of each detergent composition was evaluated according to the following method. The results are shown in Table 3.

<Method of Evaluation of Detergency>

The same evaluation method as in Test Example 2 was used except that as a soiled cloth, a commercially available cloth (EMPA 104, reflectance of the cloth before soiled=92.3%) was used and the washing temperature was altered to 40° C.

TABLE 3

| | Reflectance(%) | | Washing |
|---|---|---|---|
| | Before washing | After washing | rate (%) |
| Example 1 | 27.1 | 42.3 | 23.3 |
| Comparative Example 1 | 26.7 | 41.2 | 22.1 |
| Example 10 | 27.0 | 41.3 | 21.9 |
| Comparative Example 2 | 27.7 | 41.2 | 20.9 |

Comparative Example 3

A polyoxyethylenealkyl sulfate (trademark: Latemul D-4-D, manufactured by Kao Corporation) in which the alkyl group had 10 to 13 carbon atoms, the branching ratio was about 70% and the ethylene oxide average addition mol number was 0.6 was dried in the same method as in Example 1. However, the resulting product took not a powder form but a paste form as it was.

Comparative Example 4

A polyoxyethylenealkyl sulfate (trademark: Emal 270J, manufactured by Kao Corporation) in which the alkyl groups had 12 to 14 carbon atoms, the ethylene oxide average addition mol number was 1.9 and the ratio of adducts having an ethylene oxide addition mol number of 4 or more was 31.5% was dried in the same method as in Example 1. However, the resulting product took not a powder form but a paste form as it was.

Example 12

An anionic surfactant powder comprising a sodium polyoxyethylenealkylsulfate in which the ethylene oxide average addition mol number was 2.0 and the ratio of adducts having an ethylene oxide addition mol number of 4 or more was 19.0% was obtained in the same manner as in Example 1 except that the aqueous solution of the sodium polyoxyethylenealkylsulfate obtained in Synthetic Example 3 was used.

Example 13

An anionic surfactant powder comprising a sodium polyoxyethylenealkylsulfate in which the ethylene oxide average addition mol number was 2.0 and the ratio of adducts having an ethylene oxide addition mol number of 4 or more was 16.8% was obtained in the same manner as in Example 1 except that the aqueous solution of the sodium polyoxyethylenealkylsulfate obtained in Synthetic Example 4 was used.

Test Example 4

The caking characteristics of each of the anionic surfactant powders obtained in Examples 12 and 13 were evaluated in the same manner as in Example 1. The results are shown in Table 4.

TABLE 4

| | Alkyl composition (%) | | AS:ES weight | Ethylene oxide average addition mol | Ratio of adducts having an ethylene oxide addition mol number of 4 or | Caking |
|---|---|---|---|---|---|---|
| | C12 | C14 | ratio | number | more(%) | characteristics |
| Example 12 | 75 | 25 | 14:86 | 2.0 | 19.0 | ○ |
| Example 13 | | | 14:86 | 2.0 | 16.8 | ○ |

TABLE 4-continued

| Alkyl composition (%) | | AS:ES weight | Ethylene oxide average addition mol | Ratio of adducts having an ethylene oxide addition mol number of 4 or | Caking |
|---|---|---|---|---|---|
| C12 | C14 | ratio | number | more(%) | characteristics |

Example 14

Using a mixed solution obtained by mixing the same sodium alkylsulfate-containing paste and sodium polyoxyethylenealkylsulfate-containing aqueous solution as those used in Example 1 such that the ratio by weight of the effective components (AS:ES) was 85:15, an anionic surfactant powder comprising a sodium polyoxyethylenealkylsulfate having an ethylene oxide average addition mol number of 0.25 was obtained in the same procedures as in Example 1. 399 g (11° C.) of city water was added to a mortar powder prepared by mixing 1.2 g of this anionic surfactant powder with 1.5 kg of a powder consisting of 67% of sand, 33% of cement and 0.3% of polystyrene beads and the mixture was kneaded to obtain five batches of mortar. The specific gravity of each batch of mortar, being an index of foaming characteristics, was measured. The specific gravity is a value determined by taking the product obtained just after kneaded in a 400 cc container, weighing it and dividing the weight with 400 g. Further, the mortar was filled in a 200-mm-wide, 1000-mm-long and 20-mm-deep form to evaluate the extendibility (workability) of the mortar when applied and also to evaluate the stability of foams involved in the mortar by observing the presence or absence of cracks caused by shrinkage when the mortar was dried. The results are shown in Table 4.

Comparative Examples 5 and 6

Using a lauryl sulfate (Emal 10P-HD, manufactured by Kao Indonesia Chemicals (Corporation)) (Comparative Example 5) which was a generally used mortar foaming agent or an α-olefin sulfonate (Hostappur OSB, manufactured by Howechest) (Comparative Example 6) in place of the anionic surfactant powder in Example 14, the specific gravity of the obtained mortar was measured and the workability and the presence or absence of cracks caused by shrinkage when the mortar was dried were evaluated in the same methods as in Example 14. The results are shown in Table 5.

TABLE 5

| | | Example 14 | Comparative Example 5 | Comparative Example 6 |
|---|---|---|---|---|
| Specific gravity | First time | 1.75 | 1.74 | 1.71 |
| | Second time | 1.75 | 1.71 | 1.72 |
| | Third time | 1.77 | 1.73 | 1.69 |
| | Forth time | 1.75 | 1.71 | 1.76 |
| | Fifth time | 1.75 | 1.73 | 1.72 |
| | Average | 1.75 | 1.72 | 1.72 |
| Workability when applied | | good | Inferior | Inferior |
| Cracks when dried | | None | Present | Present |

As is clear from Table 5, although the powder of Example 14 had the same specific gravity as the powders of Comparative Examples 5 and 6, it exhibited better extendibility and higher workability than the powders of Comparative Examples 5 and 6. Also, no crack was observed when the mortar was dried. On the other hand, the powders of Comparative Examples 5 and 6 had inferior extendibility when applied to that of Example 14. Also, as to the cracks when the mortar was dried, cracks extending in a vertical direction were observed on the entire coated surface.

Example 15

A microwave dryer (manufactured by Fukae Powtec (Co., Ltd.), FMD-65JE Model) having a capacity of 65 L was charged with 20.0 kg of the sodium polyoxyethylenealkylsulfate paste obtained in Synthetic Example 5. The paste was dried and powdered under the condition that jacket temperature was 85° C., pressure was 9.3 to 6.7 kPa, the revolution of the agitator was 100 r/min and the revolution of the chopper was 3000 r/min, to obtain an anionic surfactant powder comprising a sodium polyoxyethylenealkylsulfate (average molecular weight: 311) having an ethylene oxide average addition mol number of 0.25.

Example 16

A microwave dryer (manufactured by Fukae Powtec (Co., Ltd.), FMD-65JE Model) having a capacity of 65 L was charged with 4.3 kg of an anionic surfactant powder comprising a sodium polyoxyethylenealkylsulfate (average molecular weight: 311) obtained in the same method that was used in Example 15. 20.0 kg of the sodium polyoxyethylenealkylsulfate paste obtained in Synthetic Example 5 was continuously dripped on the powder at such a rate that the powder in the drier was kept in a powder state under the condition that jacket temperature was 85° C., pressure was 6.7 kPa, the revolution of the agitator was 100 r/min and the revolution of the chopper was 3000 r/min, to obtain an anionic surfactant powder comprising a sodium polyoxyethylenealkylsulfate (average molecular weight: 311) having an ethylene oxide average addition mol number of 0.25.

Example 17

A microwave dryer (manufactured by Fukae Powtec (Co., Ltd.), FMD-65JE Model) having a capacity of 65 L was charged with 10.5 kg of a commercially available sodium alkylsulfate powder (trademark: Emal 10P-HD, manufactured by Kao Indonesia Chemicals (Corporation)). 4.9 kg of the sodium polyoxyethylenealkylsulfate paste obtained in Synthetic Example 6 was continuously dripped on the powder at such a rate that the powder in the drier was kept in a powder state under the condition that jacket temperature was 85° C., pressure was 6.7 kPa, the revolution of the agitator was 100 r/min and the revolution of the chopper was 3000 r/min, to obtain an anionic surfactant powder comprising a sodium polyoxyethylenealkylsulfate (average molecular weight: 311) having an ethylene oxide average addition mol number of 0.25.

Example 18

The anionic surfactant powder obtained in Example 16 was heated to 60° C. and continuously fed into an extrusion granulator (Domegran DG-L1 Model, 20 r/min, dice diameter: 1 mmϕ, manufactured by (Corporation) Dalton) and the resulting cylindrical granule was cooled to room temperature. Next, the granule was continuously cut using a cutting granulator (Power Mill P-02S, screen diameter: 1.5 mmϕ, manufactured by Powrex (Corporation)), followed by screening to obtain a granule having a particle diameter of 500 to 1410 μm.

Example 19

The anionic surfactant powder obtained in Example 16 was continuously fed into an extrusion granulator (Domegran DG-L1 Model, 20 r/min, dice diameter: 1 mmϕ, manufactured by (Corporation) Dalton) and the resulting cylindrical granule was cooled to room temperature. Next, the granule was cut using a cutting granulator (Power Mill P-02S, screen diameter: 1.5 mmϕ, manufactured by Powrex (Corporation)). Then, 4.0 kg of the resulting granule was placed in a High Speed Mixer (manufactured by Fukae Powtec (Co., Ltd.) having a capacity of 20 L and 60° C. hot water was circulated in a jacket to raise the temperature of the granule to 56° C. under the condition that the revolution of agitator was 150 r/min and the revolution of the chopper was 1800 r/min. Then, 12.9 g of ion exchange water was dripped on the granule in 6 minutes. After that, stirring was continued for 10 minutes in the same condition and then the granule was cooled to room temperature, followed by screening to obtain a granule having a particle diameter of 500 to 1410 μm.

Example 20 and 21

A 20 L High Speed Mixer (manufactured by Fukae Powtec (Co., Ltd.)) was charged with 1.8 kg of each of the granules of the anionic surfactant powders obtained in Examples 18 and 19. 0.2 kg of 4A type zeolite was added to the granule and the mixture was stirred at room temperature for about 3 minutes under the condition that the revolution of the agitator was 50 r/min to make the 4A type zeolite adsorb to the surface of the granule particle. The obtained each granule was screened to obtain a granule which had a particle diameter of 500 to 1410 μm and was more improved in caking characteristics.

Example 22

The sodium polyoxyethylenealkylsulfate paste obtained in Synthetic Example 5 was continuously fed into a non-contact type Sebcon (heating area: 0.3 $m^2$, manufactured by Hitachi Ltd.) kept at a heating temperature of 110° C. in the following condition: temperature: 58° C., flow rate: 13.3 kg/h, revolution: 1100 r/min and pressure: 6.7 kPa, to obtain a dry product.

Test Example 5

The caking characteristics of each granules obtained in Examples 19, 20 and 21 were evaluated according to the following method, to find that the caking characteristics of the granules of Examples 19 and 20&21 were 97% and 100% respectively.

<Caking Characteristics>

70 g of a granule was sealed in a 0.04 mm×70 mm×100 mm vinyl bag with a chuck and was kept at 50° C. for one week with applying a load uniformly to the bag by using a 7 kg weight. Then, the resulting granule was subjected to screening using a screen of JIS 1410 μm to measure the passing rate % ((weight of the passed granule/charge weight)×100) of the granule.

The invention claimed is:

1. An anionic surfactant powder comprising polyoxyalkylene alkyl ether sulfates in powder form in which the average addition mol number of alkylene oxides is 0.05 to 1 and the content of polyoxyalkylene alkyl ether sulfates provided with alkylene oxides added thereto in an amount of 4 mol or more is 30% by weight or less based on the total anionic surfactant.

2. The anionic surfactant powder according to claim 1, wherein the polyoxyalkylene alkyl ether sulfate is a compound represented by the formula (I):

$$[R^1—O(AO)_n—SO_3]_pM \quad (I)$$

wherein $R^1$ represents a straight-chain alkyl group having 8 to 20 carbon atoms, AO represents an oxyalkylene group or oxyalkylene groups having 2 to 4 carbon atoms, which may be the same as or different from one another, n denotes the average addition mol number of alkylene oxides in the range of from 0.05 to 1, M represents a cation and p represents the number of valence to M.

3. The anionic surfactant powder according to claim 1, wherein the polyoxyalkylene alkyl ether sulfate in which the average addition mol number of alkylene oxides is 0.05 to 1 comprises an alkyl sulfate in the amount of 30 to 95% by weight.

4. The anionic surfactant powder according to claim 1, further comprising a water-soluble inorganic salt.

5. A process for producing the anionic surfactant powder according to claim 1, comprising obtaining an aqueous solution or a paste comprising polyoxyalkylene alkyl ether sulfates by any of the following methods (1) to (3) and then drying and granulating them:

(1) a method in which an alkylene oxide adduct of a higher alcohol obtained by adding an alkylene oxide to a higher alcohol having 8 to 20 carbon atoms so that the average addition mol number of the alkylene oxide is 0.05 to 1 is sulfurized and neutralized;

(2) a method in which a higher alcohol is mixed with an alkylene oxide adduct of a higher alcohol so that the average addition mol number of the alkylene oxide in the mixture is 0.05 to 1 and the mixture is sulfurized and neutralized;

(3) a method in which a higher alcohol and an alkylene oxide adduct of a higher alcohol which are separately sulfurized and neutralized in advance are mixed with each other so that the average addition mol number of the mixture is 0.05 to 1.

6. A process for producing the anionic surfactant powder according to claim 1, comprising drying an aqueous solution or a paste comprising a polyoxyalkylene alkyl ether sulfate, obtained by any method of (1) to (3)

(1) a method in which an alkylene oxide adduct of a higher alcohol obtained by adding an alkylene oxide to a higher alcohol having 8 to 20 carbon atoms so that the average addition mol number of the alkylene oxide is 0.05 to 1 is sulfurized and neutralized;

(2) a method in which a higher alcohol is mixed with an alkylene oxide adduct of a higher alcohol so that the average addition mol number of the alkylene oxide in the mixture is 0.05 to 1 and the mixture is sulfurized and neutralized;

(3) a method in which a higher alcohol and an alkylene oxide adduct of a higher alcohol which are separately sulfurized and neutralized in advance are mixed with each other so that the average addition mol number of the mixture is 0.05 to 1 by any of the following methods (4) to (6) to obtain a dried product or further granulating the dried product:

(4) a method in which an aqueous solution or a paste comprising a polyoxyalkylene alkyl ether sulfate or a mixture of an aqueous solution or a paste comprising a polyoxyalkylene alkyl ether sulfate with an aqueous solution, a paste or a powder comprising an alkyl sulfate is dosed together into a batch type vacuum drier equipped with a stirring blade(s) and/or a cutter and dried at a reduced pressure;

(5) a method in which an anionic surfactant powder is placed in a batch type vacuum drier equipped with a stirring blade(s) and/or a cutter in advance to the extent that the stirring or cutting effect is obtained and then the powder is dried at a reduced pressure, supplying an aqueous solution or a paste comprising a polyoxyalkylene alkyl ether sulfate at such a feed rate that the powder of the drier may remain in the powder state;

(6) a method in which an aqueous solution or a paste comprising a polyoxyalkylene alkyl ether sulfate is dried, being fed continuously into a rotary thin film evaporator at a reduced pressure.

7. A detergent composition comprising the anionic surfactant powder according to claim 1.

8. A cement comprising the anionic surfactant powder according claim 1.

9. The anionic surfactant powder according to claim 1, wherein the content of polyoxyalkylene alkyl ether sulfates provided with alkylene oxides added thereto in an amount of 4 mol % or more is 20% by weight or less based on the total anionic surfactant.

10. The anionic surfactant powder according to claim 1, wherein the content of polyoxyalkylene alkyl ether sulfates provided with alkylene oxides added thereto in an amount of 4 mol % or more is 15% by weight or less based on the total anionic surfactant.

11. The anionic surfactant powder according to claim 2, wherein the average additional mol number of alkylene oxides is 0.1 to 1.

12. The anionic surfactant powder according to claim 2, wherein the average additional mol number of alkylene oxides is 0.2 to 0.8.

13. The anionic surfactant powder according to claim 3, wherein the alkyl sulfate is present in an amount of 50 to 90% by weight.

14. The anionic surfactant powder according to claim 4, wherein the water-soluble inorganic salt is present in an amount of 10 parts by weight or less based on 100 parts by weight of the polyoxyalkylene alkyl ether sulfates.

15. The anionic surfactant powder according to claim 4, wherein the water-soluble inorganic salt is present in an amount of 2 parts by weight or less based on 100 parts by weight of the polyoxyalkylene alkyl ether sulfates.

16. The anionic surfactant powder according to claim 1, comprising 60 to 80% by weight of an alkyl sulfate, 18 to 38% by weight of the polyoxyalkylene alkyl ether sulfate, 0.5 to 2.0% by weight of water, 0.5 to 2% by weight of an alcohol and polyoxyalkylene alkyl ether, and 1.0 to 2.0% by weight of an inorganic salt.

* * * * *